United States Patent [19]
Kuehnegger

[11] 3,945,376
[45] Mar. 23, 1976

[54] ORTHOPEDIC BRACE (ORTHESIS)

[75] Inventor: Walter Kuehnegger, Pleasant Lake, Mich.

[73] Assignee: Otto Bock Orthopedic Industry, Inc., Minneapolis, Minn.

[22] Filed: Dec. 12, 1974

[21] Appl. No.: 532,067

[52] U.S. Cl. .................................................. 128/78
[51] Int. Cl.² .......................................... A61F 5/02
[58] Field of Search ............. 128/78, 75, 87, 83, 84

[56] References Cited
UNITED STATES PATENTS

| | | | |
|---|---|---|---|
| 6,023 | 1/1849 | Mellish ................................. | 128/78 |
| 10,248 | 11/1853 | Browne................................ | 128/78 |
| 888,490 | 5/1908 | Haas ..................................... | 128/78 |
| 2,808,050 | 10/1957 | Ward ..................................... | 128/78 |
| 3,095,875 | 7/1963 | Davidson et al. ..................... | 128/78 |
| 3,771,513 | 11/1973 | Valaquez............................... | 128/78 |

FOREIGN PATENTS OR APPLICATIONS 257,376  3/1912  Germany .............................. 128/78

*Primary Examiner*—John D. Yasko
*Attorney, Agent, or Firm*—Schroeder, Siegfried, Ryan & Vidas

[57] ABSTRACT

An orthopedic brace for correction of spinal deformities is constructed forming a three dimensional space structure having a rigid pelvic band encompassing the hip portion of the pelvic region of the wearer. A pair of vertical posterior paraspinal upright members conforming to and following the general curvature of the back of the wearer at a nearly constant distance is secured at their lower ends to the pelvic band and an anterior vertical upright member conforming in general to the curvature of the chest of the wearer is secured to its lower end to the pelvic band. A sternal cross bar is fixedly secured to the upper end of the anterior upright member and a scapular cross bar is fixedly secured to the upper ends of the pair of posterior paraspinal upright members. A pair of curved shoulder bars, amply spaced from the shoulders, serve as a structural link between the sternal and scapular cross bars. A pair of flexible iliac crest members (segments) are securely fastened to an anterior (gusset type) closure plate at one end and to a posterior band at the other end. The anterior closure plate is attached to the anterior upright while the posterior band spaces and connects the posterior paraspinal uprights.

10 Claims, 6 Drawing Figures

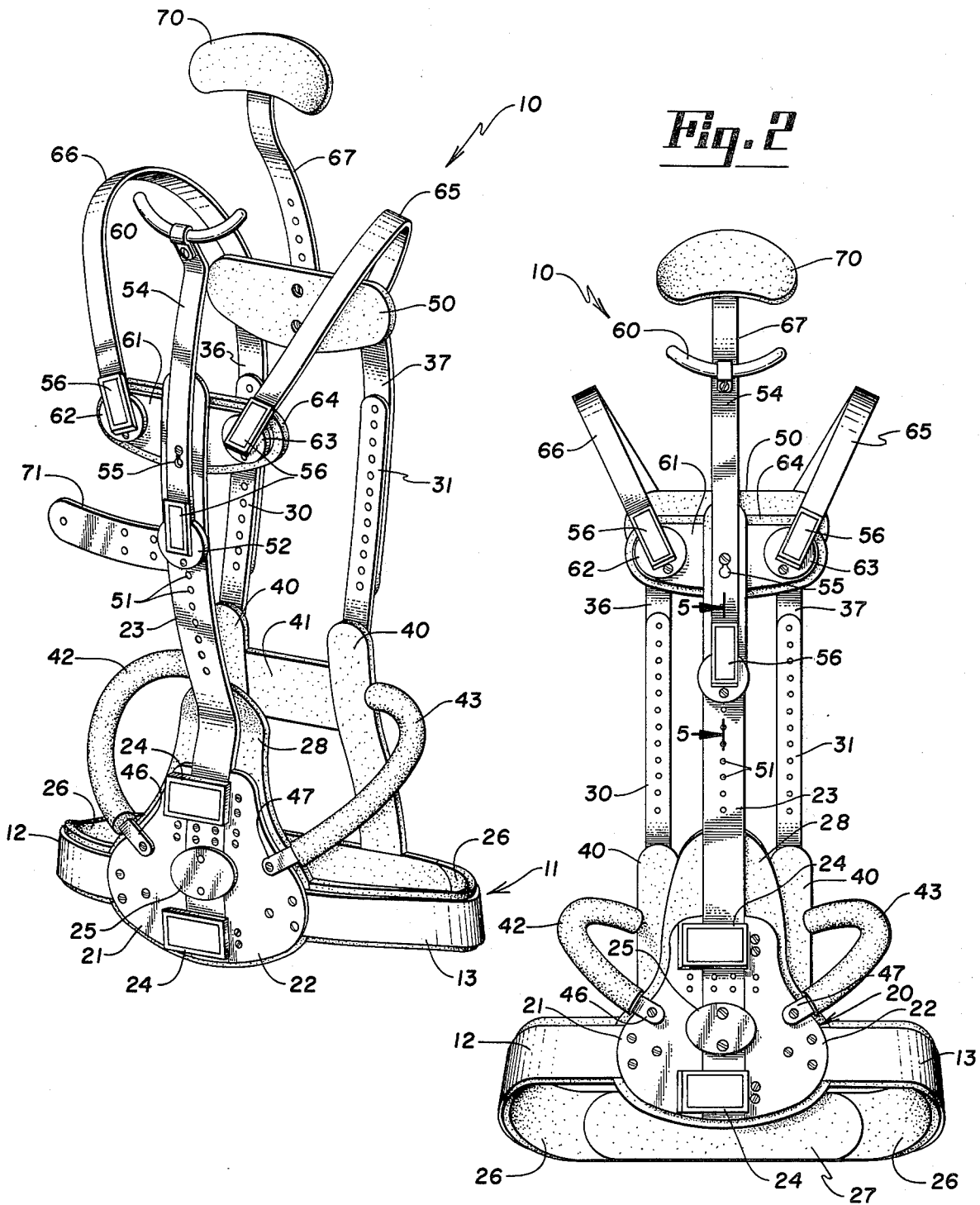

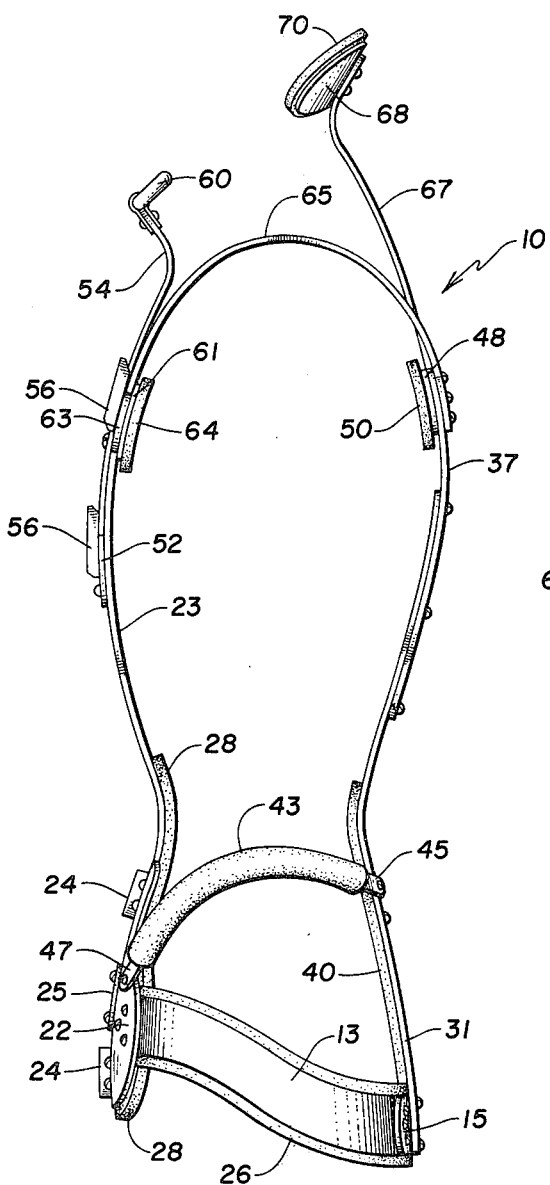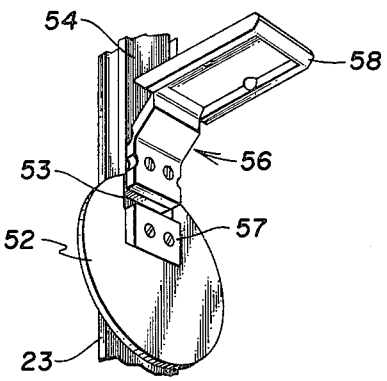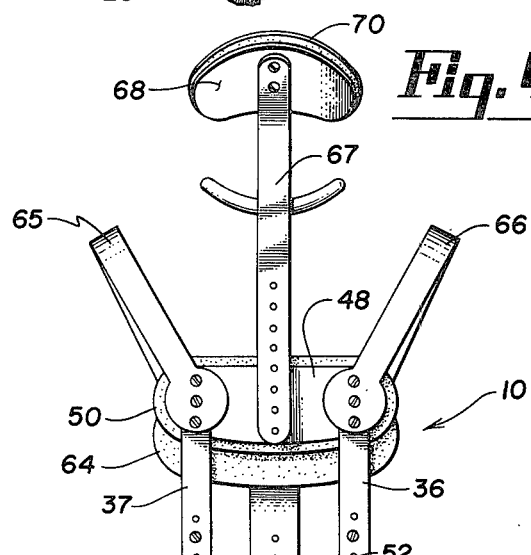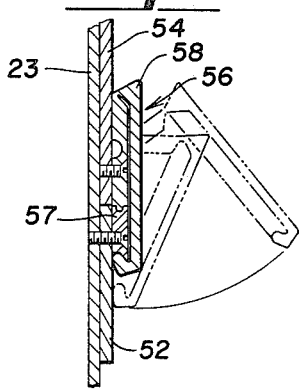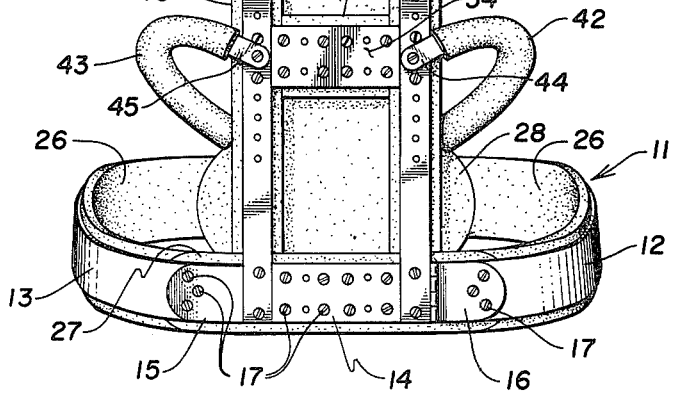

ORTHOPEDIC BRACE (ORTHESIS)

This invention relates to orthopedic braces (ortheses) for the correction of spinal deformities.

Various types of orthopedic spinal braces have been developed in attempting to correct spinal deformities of children and young adults prior to reaching their skeletal maturity. The correction of malformation due to Scoliosis, Scheuermann's Disease, and general spinal deformities in the higher thoracic region have been treated by the Milwaukee type brace. Most of the patented orthopedic spinal braces are constructed so that they are restricted to corrections or arresting spinal deformities in two planes only. One such structure may be found in U.S. Pat. No. 3,771,513. However, it is highly desirable to have an orthopedic brace that will produce corrections in an anterior-posterior direction as well as a medio-lateral direction and a thoracic derotation. In other words, spinal braces such as U.S. Pat. Nos. 2,760,486, 2,808,050, 3,331,367, 3,351,053, 3,548,817 and 443,764 do not possess the features of permitting the brace to be rigidly anchored to the pelvic section of the body to correct and arrest the rotation of the deformed spine.

The present invention makes use of a pelvic band which is hinged at one side of the posterior portion thereof to provide an anterior closure. The pelvic band works in cooperation with an iliac crest ring which is drawn firmly over the crest of the ilium of the pelvis. The anterior and posterior paraspinal upright members are joined by a sternal and scapular cross bar respectively to provide a solid anchor point for a pair of shoulder bars which are curved and amply spaced over the contour of the shoulders of the wearer. Through the use of the pelvic band and the iliac crest segments, a solid foundation of the brace is formed thus absorbing the bending moments produced by any of the lateral pads of the brace itself. Through the application of lateral pad pressure, force components are developed which aid in fitting and anchoring the pelvic section as well as distending and straightening the spinal column. Through the use of the rigid frame, attachment points are available for pads which may be used to apply physical pressure upon or near the apex of deformities of the spine for the purpose of arresting or correcting the deformed spinal column. In addition, provision is made to releasably secure a mandibular retention bar in cooperation with an occipital support at the posterior of the brace.

It is therefore a general object of this invention to provide an improvement in a brace which may be used in the treatment of the spine requiring correction in three planes.

It is a more specific object of this invention to provide an improved brace which is capable of correcting or arresting the severe spinal deformity involving an element of rotation of the spine.

It is yet another object of this invention to provide an improved brace for the treatment of the spine which has a pelvic band and iliac crest rings cooperating to form a rigid lower anchor structure for the brace.

It is still a further object of the present invention to provide an improved brace for the treatment of the spine in which the brace has an anterior closure.

It is a more specific object of this invention to provide an improved brace for the treatment of the spine which is capable of fitting male and female patients from age 8 through 18.

It is another object of this invention to provide an improved brace for treatment of the spine having a pair of iliac crest segments which constantly align with the anatomical changes from sitting to standing and vice versa including the growth of the wearer.

These and other objects and advantages of the invention will more fully appear from the following description, wherein like reference characters refer to the same or similar parts throughout the several views, and in which:

FIG. 1 is a perspective view of the improved brace which shows an outrigger member for the purpose of attaching pressure pads directly or by straps indirectly;

FIG. 2 is a front elevation of the improved brace;

FIG. 3 is a side elevation of the improved brace;

FIG. 4 is a back elevation of the improved brace;

FIG. 5 is a sectional view of a draw latch mechanism taken along lines 5—5 of FIG. 2; and FIG. 6 is a perspective view of the draw latch mechanism shown in FIG. 5.

Referring now principally to FIGS. 1 through 4, an orthopedic brace 10 is disclosed which has a pelvic band 11 located at the lower extremity of brace 10. Pelvic band 11 is formed in three parts, a right segment 12, and a left segment 13, which is joined by an intermediate posterior plate member 14. Pelvic segment 13 is secured to an auxiliary band 15 and pelvic segment 12 is secured to a pelvic band hinge 16. Suitable means such as screws or rivets 17 may be used to secure the various pieces to each other in a fixed relationship. It will generally be found that machine screws are preferable in locations that require reconstructions and growth adjustment so as to ensure a minimum of effort in releasing members which have been joined together.

An anterior closure (gusset) plate 20 is formed from two flat sheet members 21 and 22 which have a general outline like that of a pear, the two members being joined respectively to pelvic band segments 12 and 13. Disposed between anterior closure plate members 21 and 22 is an anterior upright member 23. A pair of anterior closure bracket members (not shown) are secured behind anterior upright member 23 and through the use of securing means 17, anterior closure plate member 22 is secured to anterior upright member 23. Anterior upright member 23 is formed to depress the abdominal region and is extended outwardly in a gradual manner until it no longer engages the body at a location approximately 1 to 2 inches below the xiphoid of the patient. Pelvic band segments 12 and 13 are secured to the flaired out portion of closure plate members 21 and 22, thus completing the pelvic band 11.

The pelvic band is form fitted around the buttocks of the patient and passes laterally between the anterior superior iliac spine and the greater trochanter of the femur. The contours of pelvic band 11 follow the anatomical outline of the patient and provide sufficient clearance for sitting. The pelvic band 11 is smoothly curved to join the posterior and anterior upright members 30, 31 and 23 respectively. The posterior members 30 and 31 extend downwardly over the gluteal region of the hips while the anterior upright member 23 sufficiently clears the superior margin of the pubic bone of the pelvis.

To facilitate the opening and securing pelvic band member 12 with respect to anterior upright member 23, a pair of releasably engagable draw latch mechanisms 24 are secured to anterior upright member 23 and have a keeper member (not shown) secured to anterior closure plate member 21. Draw latch mechanisms 24 are shown in more detail in FIGS. 5 and 6 and will be described in further detail with reference to FIGS. 5 and 6. For further details relative to draw latch mechanism 24, reference is made to U.S. Pat. No. 3,181,905 which describes such a mechanism that is available from Southco, Inc., Lester, Pa., as part No. 07-10-201-11.

Through the use of draw latch mechanisms 24, one of which is disposed at the bottom of anterior closure plate 20 and the other of which is disposed near the top portion of anterior closure plate 20, pelvic band 11 is thus permitted to be opened anteriorly. It will also be observed that through the reversal of hinge No. 16 and pelvic band member 15, the mechanism may be designed to open from the opposite side through the reversal of draw latch mechanisms to accommodate the common practice of the differences between male and female clothing.

To help facilitate bringing anterior closure plate members 21 and 22 into conforming alignment with upright member 23, a tab guide 25 is secured to the front of upright member 23. Tab guide 25 is much like an elliptical disc and thus helps to align members 21 and 22 in cooperation with the anterior bracket members (not shown).

It has been found that pelvic band member 11 is preferably made from sheet aluminum material which is generally 1.5 inches wide and 0.063 inches thick. The anterior closure plate members 21 and 22 are formed of the same type of material as are the other metal portions of the brace yet to be described. A pair of pelvic band pads 26 are secured on the inner sides of pelvic band members 12 and 13, and an intermediate pad 27 is secured over the ends of pads 26 and on the inner side of the posterior pelvic band members. The padding may be made from foam plastic or a leather/-plastic combination.

A pad 28, formed of similar material and slightly larger than the outline of the anterior closure plate, is secured on the inner side thereof, one side of which is not secured to plate members 21 and 22 so that in opening pelvic band 11, pad 28 will remain secured to the remainder of the brace mechanism. Pad 28 in cooperation with the anterior closure plate may depress the abdomen of a 15 year old wearer a maximum of 1½ inches to produce intra-abdominal pressure for correction of the spine.

A pair of posterior paraspinal upright base members 30 and 31 are secured at their lower ends to pelvic band member 12 and hinge 16 and to pelvic band member 13 and member 15 respectively. It will be observed that a series of machine screw holes 32 and 33 respectively are formed vertically within the posterior upright base members 30 and 31. In a similar fashion, a plurality of screw holes are formed laterally along member 14 so that the pelvic band member 11 may be enlarged. An upper posterior adjustment plate 34 is secured between upright members 30 and 31 by suitable means such as screws 17 through the use of a pair of auxiliary plates (not shown) which are secured on the inner side to upright members 30 and 31 and to upper posterior adjustment plate 34 to form a solid brace mechanism.

A pair of posterior upright extension members 36 and 37 are secured to posterior upright base members 30 and 31 respectively by suitable means such as screws 17 and are adjustable vertically through the use of a plurality of screw holes 38 and 39 formed longitudinally along upright extension members 36 and 37. The latter will facilitate readjustment for patient growth.

A pair of upright posterior pads 40 are secured to posterior upright base members 30 and 31 on the inner side thereof and another pad 41 extends transversely across upper posterior adjustment plate 34 on the inner side thereof, the pads being formed of the same material as that described previously.

A pair of iliac crest segments 42 and 43 are pivotally secured to posterior upright base members 30 and 31 respectively through the use of a pair of angle brackets 44 and 45 respectively. Brackets 44 and 45 are secured to the upright base members through the use of suitable means such as machine screws 17. Iliac crest segments 42 and 43 are generally formed of a flexible material such as a rubber hose having an outer diameter of 0.75 inches and an inside diameter of 0.25 inches. To secure the iliac crest segments 42 and 43 to angle brackets 44 and 45 respectively, a pair of anchor members (not shown) are inserted within the ends of the iliac crest segments and anchored thereto. One such anchor which is found to be suitable is that of a hollow wall screw anchor which has an outer diameter of 0.25 inches and is approximately 1.80 inches long, and is manufactured by the Star Expansion Company of Mountainville, N.Y. as part No. 2705-00300. Upon tightening the screw of the anchor mechanism, ribs of the anchor are expanded to engage the walls of the tubing, thus providing a gripping action. A pair of angle brackets 46 and 47 are respectively secured to iliac crest segments 42 and 43 and are anchored in the same manner as the angle brackets at the posterior portion of brace 10.

The upper anchor point of the pelvic section of the brace is created through the use of a pair of iliac crest segments 42 and 43 which are pulled firmly over the crest of the ilium of the pelvis. The two ring segments are attached posteriorly to the two posterior upright base members 30 and 31 and are secured firmly over the crest of the ilium by the attachment to the anterior closure plates 21 and 22, thus forming a solid metal-to-metal connection.

A scapular cross bar 48 is secured to the upper ends of the posterior upright extension members 36 and 37 through suitable means such as machine screws 17 to complete the rigid structural frame on the posterior portion of the brace. It will be noted that the posterior upright members are bent to conform to the general curvature of the back of the wearer and disposed therefrom with a near constant spacing.

A pad 50 is secured on the inner side of scapular cross bar 48 and is formed of the same material as that previously described for the other pad members.

Anterior upright member 23 has a series of machine screw holes 51 formed therein longitudinally along the upper portion of member 23. A guide disc 52 is secured to member 23 through suitable means such as screws 17 and contains a notched portion 53 in the upper portion thereof (FIG. 6).

A mandibular retention member 54 is secured to the anterior upright member 23 through the use of a slotted hole like a keyhole 55 through which a screw passes and is anchored in member 23. The bottom end of retention member 54 is anchored in notch 53 and is held in place through the use of a draw latch mechanism 56 which is slightly smaller than draw latch mechanism 24 but operates in the same manner. Reference is now made to FIGS. 5 and 6 for further explanation of the latch mechanism. Draw latch mechanism 56 includes a latch keeper 57 which is secured on the outer portion of guide disc 52 by machine screws or other suitable means and a latch hasp 58 is secured to the mandibular retention member 54 at the end thereof through suitable means such as screws or rivets. The latch hasp 58 and the keeper 57 are formed from polypropylene material and thus a hinge portion is secured to a lid portion forming part of the hasp so that the latch may be snapped into place and locked as shown in FIG. 5. The other positions shown in the dashed lines show the open position. As indicated previously, a further description of the latch may be found in U.S. Pat. No. 3,181,905.

A mandibular retention bar 60 is secured at the upper end of retention member 54 where the support member is formed somewhat at right angles with the anterior upright member 23 to inductively retain the lower portion of the jaw. A plastic vinyl cover or sleeve is fitted over member 60 to avoid the metal contact with the jaw.

A sternal cross bar 61 is secured transversely to anterior upright member 23 through suitable means such as screws near the upper end of member 23. Sternal cross bar 61 has a pair of guide discs 62 and 63 secured thereto through suitable means such as screws or rivets. Guide discs 62 and 63 are identical to guide disc 52 with the notch in the upper portion being angled upwardly and outwardly in a lateral manner. The sternal cross bar pad 64 is secured on the inner side of sternal cross bar 61, the pad being formed to overlap the general outline of cross bar 61 and of the same material as described previously for the pads used with the brace. Scapular pad 50 and sternal pad 64 are spaced so as not to contact the patient contour in the erect standing and sitting posture.

A pair of shoulder bars 65 and 66 are secured respectively to posterior upright extension members 37 and 36 as well as the ends of scapular cross bar 48. That is, shoulder bars 65 and 66 extend upwardly and outwardly at an angled position from cross bar 48 in a curved fitting relationship at a near parallel spacing to the contour of the shoulders of the wearer providing a gap of approximately 30mm for patient growth at the highest point of the shoulder. The front portions thereof extend into the notched portions of guide discs 63 and 63 respectively. To secure shoulder bars 65 and 66 to sternal cross bar 61, another pair of draw latch mechanisms 56 are used at the ends of the shoulder bars in the same manner as described previously in securing the mandibular retention member 54 to anterior upright member 23. Shoulder bars 65 and 66 are also formed of aluminum sheet or bar material which is 0.125 inches thick and 0.75 inches wide.

Secured midway between posterior upright extension members 36 and 37, is an occipital support member 67 held by suitable means such as screws 17. Support member 67 extends upwardly where the end portion is bent at a near right angle to support an occipital plate 68. The plate member is formed of aluminum sheet material having a thickness of 0.063 inches and is bent to conform to the occipital portion of the head of the wearer. A pad 70 is secured thereto and is formed of the same material and the same thickness as the pads described previously.

In some applications, it may be desirable to apply pressure to certain portions of the body and an outrigger member 71 may be attached to the different members of the brace 10. Outrigger member 71 is shown in FIG. 1 as being secured to the anterior upright member 23. In this application, a commercially available thoracic pad (not shown, because of many different configuration possibilities) is placed over the deformed rib hump and attached anteriorly to the outrigger member 71 and posteriorly to one of the paraspinal upright members 36 or 37 by an adjustable strap made from leather, nylon or such.

It will be found that the use of the brace disclosed herein will provide an anchor at the pelvic section of the wearer for the erection of a solid thoracic and cervical structure. This structure provides attachment points for pads which in turn may exert physical pressure upon or near the apex of the deformities of the spine of the wearer for the purpose of arresting or correcting the malformation. It will be found that the brace also possesses additional sought after features in that the pelvic section is designed to produce intra-abdominal pressure to aid the straightening of the lumbar region of the spinal column. At the upper end of the brace, the mandibular retention bar inductively reminds the patient to stretch and further straighten the spinal column while the occipital support maintains the alignment of these actions in the desired direction.

The orthopedic brace disclosed herein permits the wearer to easily don or doff the orthopedic brace due to the releasable latch members and yet retain the rigidity needed while being worn. Through the removability of the mandibular retention bar and support member, the wearer is not restricted during eating, putting on shoes, driving an automobile, or donning or doffing the brace. The flexible iliac crest segment is constantly aligned with the growth of the patient while being kept tight over the pelvic section.

It will, of course, be understood that various changes may be made in the form, details, arrangement and proportions of the parts without departing from the scope of the invention which consists of the matter shown and described herein and set forth in the appended claims.

What is claimed is:

1. An orthopedic brace for correction of the spinal deformities comprising:
    a. a rigid pelvic band constructed and arranged to engage in close contour fitting relationship, the anterior, posterior and lateral hip portions of the pelvic region of a wearer;
    b. a pair of posterior paraspinal upright members conforming to the general curvature of the back and pelvic region of a wearer, said paraspinal upright members being spatially disposed from each other and fixedly secured to said pelvic band at their lower ends;
    c. an anterior upright member fixedly secured to said pelvic band at its lower end and formed so as to engage the abdominal region and gradually extend upwardly and outwardly to clear the xiphoid of the patient and follow the general anterior curvature in spatially disposed relationship;
    d. a sternal cross bar fixedly secured to the upper end of said anterior upright member;
    e. a scapular cross bar fixedly secured to the upper ends of said pair of posterior upright members;

f. a pair of rigid shoulder bars rigidly secured to the ends of said sternal and scapular cross bars and extending in curved, spatially disposed relationship to the contour of the shoulders of a wearer;

g. and a pair of flexible iliac crest members pivotally secured at each end thereof between said anterior and posterior uprights, the ends of said iliac crest members being disposed vertically above said pelvic band whereby said brace forms a three dimensional space structure.

2. The structure set forth in claim 1 including:

h. a pelvic band hinge having one member thereof secured to one of said posterior upright members and having the other member extending outwardly therefrom;

i. said pelvic band being formed in two segments, one of which is secured to said outwardly extending hinge member on one end and releasably secured to said anterior upright member on the outer end thereof.

3. The structure set forth in claim 1 including:

a mandibular retention member constructed and arranged to inductively engage the soft tissue under the lower jaw of the wearer and having a lower support portion releasably secured to said anterior upright member;

and an occipital support member constructed and arranged to engage the head of the wearer at the lower occipital region and having a lower support portion fixedly secured to said scapular cross bar.

4. The structure set forth in claim 2 wherein said anterior upright member includes a closure plate formed in two parts disposed in substantially the same plane as said anterior upright member and said rigid pelvic band, said closure plate parts secured to said anterior upright and said rigid pelvic band.

5. The structure set forth in claim 4 including:

a plurality of releasably engageable draw latch mechanisms securing said pelvic band segment and closure plate to said anterior upright member at the lower portion of said brace, and securing said shoulder bars and mandibular retention member to said anterior upright member at the upper portion of said brace.

6. The structure set forth in claim 1 including:

an outrigger member constructed and arranged to be attached in a laterally extending manner to one of said anterior or posterior upright members for the purpose of providing rigid direct and indirect attachment points for at least one pad as determined by the individual patient malformation.

7. The structure set forth in claim 4 including:

a plurality of lining pads constructed and arranged to engage the body of the wearer of said brace, said pads being secured to the inner portions of said pelvic band, said posterior and anterior upright members including said closure plate, said sternal and scapular cross bars, and said occipital support.

8. The structure set forth in claim 6 including:

pressure and retention pads secured to at least one, of said outrigger member, said anterior and posterior paraspinal upright members, said pads being constructed and arranged to apply pressure to the body of the wearer to arrest or correct the individual deformity.

9. The structure as set forth in claim 1 wherein said anterior upright member is shaped to extend outwardly and upwardly starting approximately 1 to 2 inches below the xiphoid of the patient and conforming to the general anterior curvature of the patient at approximately ½ inch spacing therefrom.

10. The structure as set forth in claim 1 wherein said pair of rigid shoulder bars having a maximum clearance of substantially 30 mm at the highest portion of the shoulder of the wearer.

* * * * *